(12) United States Patent
Rustum et al.

(10) Patent No.: US 7,744,854 B2
(45) Date of Patent: Jun. 29, 2010

(54) METHOD FOR OPTIMIZING CANCER THERAPY BY MONITORING MATURATION OF TUMOR ASSOCIATED VASCULATURE BY SELENIUM

(75) Inventors: Youcef M. Rustum, Amherst, NY (US); Arup Bhattacharya, Amherst, NY (US); Karoly Toth, N. Amherst, NY (US); Harry K. Slocum, Buffalo, NY (US); Rami G. Azrak, Getzville, NY (US); Sreenivasulu Chintala, Amherst, NY (US); Mukund Seshadri, Buffalo, NY (US); Richard Mazurchuk, Clarence, NY (US)

(73) Assignee: Health Research, Inc., Buffalo, NY (US)

( * ) Notice: Subject to any disclaimer, the term of this patent is extended or adjusted under 35 U.S.C. 154(b) by 598 days.

(21) Appl. No.: 11/728,075

(22) Filed: Mar. 23, 2007

(65) Prior Publication Data

US 2008/0019919 A1 Jan. 24, 2008

Related U.S. Application Data

(60) Provisional application No. 60/785,935, filed on Mar. 24, 2006.

(51) Int. Cl.
A61B 5/055 (2006.01)
A61K 31/44 (2006.01)
A61K 31/28 (2006.01)
A61K 31/095 (2006.01)
A61K 31/505 (2006.01)
A61K 33/24 (2006.01)
A61K 49/00 (2006.01)
A01N 37/12 (2006.01)
A01N 43/02 (2006.01)

(52) U.S. Cl. .................... 424/9.3; 424/9.1; 424/649; 514/561; 514/34; 514/269; 514/283; 514/492; 514/449; 435/40

(58) Field of Classification Search .................. None
See application file for complete search history.

(56) References Cited

OTHER PUBLICATIONS

Bhattacharya et al. Proc. Am. Assoc. Canc. Res. Ann. Mtng. (Apr. 2006) vol. 47, 413-414.*
Cao et al. Clin. Canc. Res. 10: 2561-2569, 2004.*
Fakih, M.G. et al, A Phase I and Pharmacokinetic Study of Fixed-Dose Selenomethionine and Irinotecan in Solid Tumors, Clinical Cancer Research, Feb. 15, 2006, 1237-1244, vol. 12(4).

* cited by examiner

*Primary Examiner*—Christine J Saoud
(74) *Attorney, Agent, or Firm*—Hodgson Russ LLP

(57) ABSTRACT

This invention provides a method for a method for optimizing the regimen for the administration of chemotherapeutic agents. The method comprises administration of a selenium compound to an individual, monitoring the modulation of tumor vessel maturation (TVM) to identify an optimal time for administration of a chemotherapeutic agent. This invention also provides a method to determine whether or not a tumor is likely to be a responder to chemotherapy. The method comprises administration of a selenium compound to an individual and determining whether or not an increase in TVM is observed. An increased TVM following administration of selenium is an indication that the tumor will likely respond the chemotherapy.

11 Claims, 9 Drawing Sheets

US 7,744,854 B2

METHOD FOR OPTIMIZING CANCER THERAPY BY MONITORING MATURATION OF TUMOR ASSOCIATED VASCULATURE BY SELENIUM

This application claims priority to U.S. Provisional application No. 60/785,935, filed on Mar. 24, 2006, the disclosure of which is incorporated herein by reference.

FIELD OF THE INVENTION

This invention relates generally to the field of cancer and more particularly to treatment of solid tumors involving monitoring of tumor vessel maturation by selenium for optimizing the effect of chemotherapeutic agents.

BACKGROUND AND SIGNIFICANCE OF INVENTION

Solid tumor malignancies accounts for 85% cancer mortality that in 2004 was responsible for 23% of all deaths in US. Current approaches for the treatment of solid tumor malignancies with established agents and with the new targeted agents used alone and in combination are limited, in part, by inability to deliver cytotoxic agents selectively to the tumor tissue in sufficient concentrations critical for tumor cell kill that translate into meaningful and durable responses. Evidence of this limitation is derived from the following: 1) response of solid tumor malignancies to existing therapy are relatively poor and don't provide long and sustained cures; 2) drug concentration used in vitro (in culture in test tube) to produce significant growth inhibition that correlates with inhibition of specific target and/or pathways is difficult to achieve in tumor cells in vivo (whole organism—animal or human) at their recommended doses without significant organ-specific toxicity; 3) effective modulation of molecular and genetic profile by cytotoxic agents that can be easily achieved in vitro but not in vivo; 4) treatment with cytotoxic agents can produce significant toxicity against normal organs, but not against tumor tissues. These results clearly indicates that though blood cytotoxic concentrations are achieved with the recommended cytotoxic doses; the delivery to tumor tissues represents a major therapeutic limitation regardless of the molecular profile of tumor cells.

It is now well established that tumors need continuous supply of nutrients and oxygen in order to grow. This is typically achieved by formation of new tumor vasculature. Therefore, antiangiogenic therapies have been considered in the treatment of tumors. Current antiangiogenic agent use, however, is fraught with various problems and new antiangiogenic techniques are needed. Another important determinant of tumor aggressiveness is tumor microvessel density. However, chemotherapeutic agents are often used without a consideration of the role tumor microvessel density (TMD) plays. Thus, there is a need in the field of cancer therapy for therapeutic approaches which take into consideration the modulation of tumor vasculature.

SUMMARY OF THE INVENTION

The present invention provides a method for optimizing the regimen for the administration of chemotherapeutic agents. The method is based on the observation that selenium compounds such as methylselenocysteine (MSC) and seleno-L-methionine (SLM) enhance the maturation of existing tumor blood vessels while inhibiting the development of new blood vessels. Accordingly, the method comprises administration of a selenium compound to an individual, monitoring the modulation of tumor vessel maturation (TVM) to identify an optimal time for administration of a chemotherapeutic agent.

In another embodiment, a method is also provided to determine whether or not a tumor is likely to be a responder to chemotherapy. This method comprises the steps of administration of a selenium compound to an individual and determining whether or not an increase in TVM is observed. An increased TVM following administration of selenium is an indication that the tumor will likely respond to the chemotherapy.

DETAILED DESCRIPTION OF THE INVENTION

Figure 1:
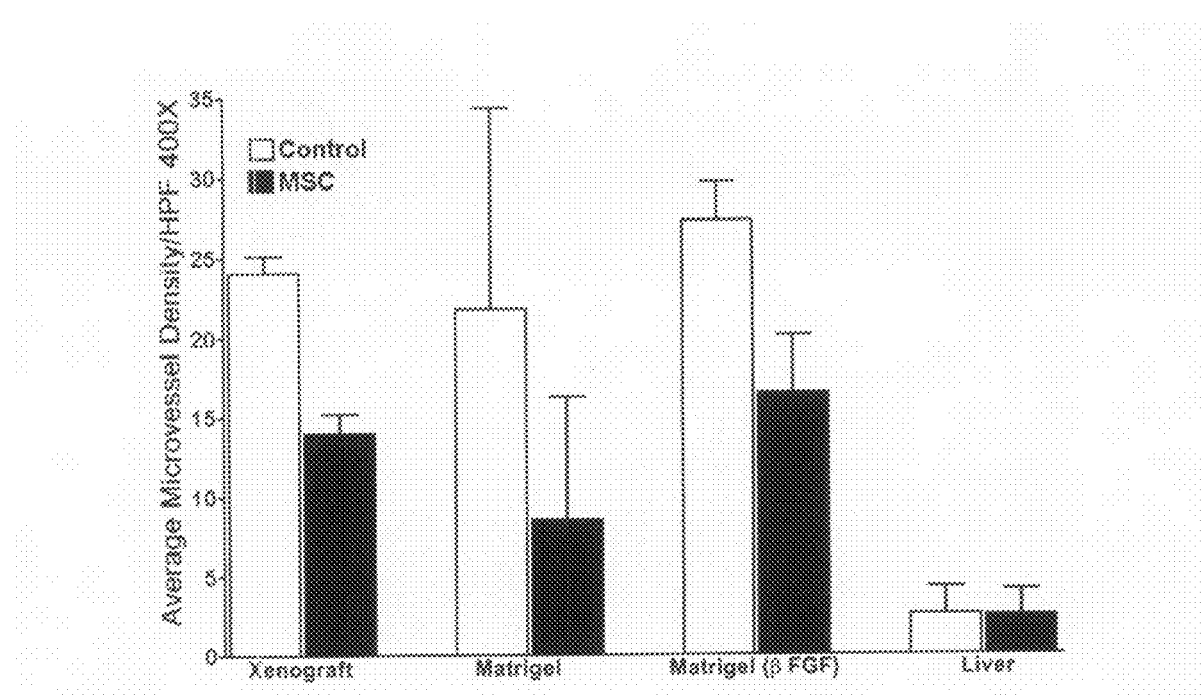
FIG. 1. Antiangiogenic effect of MSC in various in vivo systems

The present invention is based on the observation that selenium promotes TVM. Use of selenium for priming the tumor for vascular maturation with cancer therapy can potentially impact cancer therapy. The present invention can also be used for monitoring of the therapy outcome in patients with different malignancies including gastrointestinal, prostate, colorectal, lung, head and neck, hematological malignancies and ovarian cancer. TVM induced by administration of selenium can be used in combination with different anticancer drugs belonging to various diverse classes of anti-cancer drugs.

Our results indicate that, selenium causes vessel arborization, pruning and maturation, retarding the formation of new vessels while 'normalizing' the existing vessels for better drug delivery. Selenium induced tumor vascular normalization can be the basis for selective therapeutic enhancement multiple chemotherapeutic agents independent of tumor types or drug type. The result generated can provide a basis for developing new and novel approaches for treating solid tumor malignancies.

The method of the present invention comprises administration of a selenium compound, monitoring of TVM, identifying a time when the selenium has a significant effect on TVM and then administering the chemotherapeutic agent. In one embodiment, degree of TVM can be evaluated before the selenium administration and monitored at different times after initiation of administration. Upon detection of an effect, the chemotherapeutic agent can be administered. An effect can be easily identified by those skilled in the art. An effect may be detected visually or may be calculated using various parameters. Any detectable effect (such as a 5-10% effect) may be used to initiate the administration of the chemotherapeutic agent. In one embodiment, TVM can be modulated after 3 days of selenium administration and the monitoring can be continued up to 21 days. Once the optimal administration time for a chemotherapeutic agent for a particular individual is determined, the same schedule can be followed for subsequent chemotherapeutic agent administrations without the need for monitoring of TVM.

In another embodiment, the present invention also provides a method to determine whether or not a tumor is likely to be a responder to chemotherapy. This method comprises the steps of administration of a selenium compound to an individual and determining whether or not an increase in TVM is observed. An increased TVM following administration of selenium is an indication that the tumor will likely respond to the chemotherapy.

TVM can be determined by a variety of methods known in the art. For example, TVM can be measured by immunohistochemical methods to detect various markers of vascular maturation, including pericytes containing α-smooth muscle actin (SMA). The effect of selenium on TVM and tumor vascular function can also be assessed using various imaging techniques including magnetic resonance imaging (MRI)— (see Strecker et al., 2003, *International Journal of Clinical Pharmacology and Therapeutics*, 41:603-605; No. 12). MRI technology provides a non-invasive approach for kinetic assessment of the effects of treatment on tumor associated microvessel density and function. MR imaging techniques, including dynamic contrast enhanced (DCE) MR imaging, apparent diffusion coefficient (ADC) mapping and blood oxygen level dependent (BOLD) functional MR (fMR), have been developed for non-invasive longitudinal characterization of tumor microvasculature and micro environmental parameters. The utility of MRI at 4.7T for assessing intratumor vascular status with immunohistochemistry validation has been demonstrated (Bhattacharya et al., 2004, Clin Cancer Res., 10:8005-8017). MRI is a versatile technique that is used experimentally and clinically to characterize tumor microvasculature. Several parameters such as vascular volume, permeability, perfusion and oxygenation have been successfully assessed using MRI. Contrast-enhanced MRI is an extremely useful imaging technique that is extensively used in preclinical and clinical studies for the assessment of antivascular and antiangiogenic therapies. The ability to serially assess tumors by 4.7T MR at various times during and after treatment could significantly aid in identifying tumor vasculature. The non-invasive nature of the technique combined with its multislice capabilities allows simultaneous visualization of tumor and normal tissues.

Alternatively, other markers on selenium's effect on TVM can be used. We have observed that molecular markers associated with angiogenesis, namely iNOS, Cox-2, HIF-1α and vascular endothelial growth factor (VEGF) expression were significantly down-regulated by the selenium/irinotecan combination. Down-regulation of molecular markers associated with angiogenesis were observed optimally on day 14 of daily treatment—which would be indicative of the optimal time for scheduling of weekly therapy with irinotecan. These data suggest that selenium sensitizes tumor cells to subsequent treatment with irinotecan. Our data demonstrates that selenium reduced total blood vessel density and leads to tumor vascular maturation through increased recruitment of α-smooth muscle actin containing pericytes to the remaining immature vessels. Also, our results revealed that selenium down regulated Delta4 (DLL4), ligand for Notch4, which is required for the abnormal/or remodeling of tumor vasculature. Down-regulation of DLL4 leads to normalization of tumor vasculature (REF). Based on these results, the present invention provides a method for optimizing administration of chemotherapeutic agents.

Selenium compounds useful for the present invention are organic forms since these are known to be less toxic. Examples of preferred selenium compounds include among others methylselenocysteine (MSC) and seleno-L-methionine (SLM). The doses of selenium compounds are in the range of about 200 µg/person/day to about 7.2 mg/person/day and maybe administered daily for up to 1 year or longer. It has been reported that up to 2200 µg/patient/day is generally considered to be safe without associated toxicity (Fakih, M. G. et al, Clinical Cancer Res, 2006; 12 (4), 1237-44).

This invention is useful for monitoring TVM with anticancer agents including fluoropyrimidines, pyrimidine nucleosides, purines, platinum analogues, antroacyclines, podophyllotoxins, camptothecins, hormones and hormone analogues, enzymes, proteins and antibodies, vinca alkaloids, taxanes. The anti-cancer agents for the present invention generally fall into one or more of the following functional categories: antihormones, antifolates, antimicrotubule agents, alkylating agents, antimetabolites, antibiotics, topoisomerase inhibitors and antivirals. While the present method for augmenting antitumor activity is applicable for any chemotherapeutic agent, some exemplary ones are irinotecan, 5-fluorouracil (FU), taxol, cisplatin, doxorubicin, oxaliplatin, cyclophasphamide, and EGF and VGF inhibitors.

In the present invention one or more chemotherapeutic agents may be used accordingly to the criteria well known in the art of cancer chemotherapeutics. The dosage and administrative regimens of the chemotherapeutics are well within the purview of those skilled in the art. Selenium administration is initiated before the start of chemotherapy, preferably at least 5 days before the start of chemotherapy and more preferably between 7 to 14 days prior to start of chemotherapy. By monitoring TVM, the chemotherapeutic agent can be administered at a time when selenium has optimally stabilized established tumor vasculature which therefore becomes capable of delivering greater cytotoxic agents in the tumor, sufficient to produce the desired therapeutic benefit. The selenium administration can be continued during chemotherapy.

EXAMPLE 1

This example demonstrates the antiangiogenic effect of MSC. Data in FIG. 1 provides evidence that selenium (0.2 mg/mouse/day) decreases the intratumoral microvessel density (MVD) in both FaDu xenografts after 2 weeks, and, also in matrigel plug (implanted subcutaneously, s.c) containing cultured FaDu tumor cells ($10^6$ cells) after 1 week of selenium treatment. Selenium showed a similar antiangiogenic effect on the proliferating mouse endothelial cells in the standard in vivo matrigel plug assay containing bFGF but no tumor cells. Microvessels were counted based on endothelial cells immunostaining with CD31 Mab on paraffin sections, after zinc fixative ($p<0.05$ in each system). We demonstrate that (i) FaDu xenografts had a similar decrease (~30%) in MVD after the synergistic combination treatment (irinotecan/selenium)

as compared to irinotecan alone, and, (ii) this reduced angiogenesis is correlated with down regulation of pro-angiogenic markers such as Cox-2, iNOS, HIF-1α expression. In addition, selenium down regulates the expression (WB) and secretion (ELISA) of VEGF in FaDu tumor cells in vitro after combination treatment with SN-38. VEGF secretion was decreased with selenium alone in this in vitro model. CD31/Tunnel double staining did not show apoptotic endothelial cell nuclei in the angiogenic microvessels; thereby indicating that apoptosis is unlikely to be involved as a mechanism in the reduction of microvessels. The histopathological studies did not show any signs of other direct antivascular effect such as microvessel necrosis, endothelial cell death or microthrombus formation. Thus, selenium inhibits proliferation of endothelial cells. Further, these antiangiogenic effects of selenium are specific for tumors since normal tissues/organs studied such as liver does not show any effect of selenium on normal vasculature. Data generated to date observed reduction of microvessel density by selenium is unlikely the result of induced apoptosis, rather the result of inhibition of endothelial cell proliferation that could result in preventative vessel branching, which are presumed leaky and unstable. Thus effect of MSC is evident on any neoangiogenesis process. MSC does not show any antiangiogenic properties on normal tissues such as liver as shown in FIG. 1. These data indicate that selenium did not induce the formation of detectable new blood vessels, but does not damage existing normal vasculature.

EXAMPLE 2

This Example demonstrates the use of fMR imaging as an initial prognostic marker of therapy response. Mice bearing bilateral HNSCC xenografts A253 were treated with MSC (started on day-7) for a total of 35 days and CPT-11 administered at MTD of 100 mg/kg i.v. weekly×4. BOLD fMR imaging done at various time points during therapy as follows to determine prognostic significances of therapeutic response in tumors that responded completely vs. those that did not have a complete regression.

Mice were anesthetized with 100 mg/kg ketamine HCl/10 mg/kg xylazine (intraperitoneally) and imaged with T2*-weighted spin echo-based rapid acquisition with refocused echoes (RARE) imaging sequence (Echo time=79.7 ms, Repetition time=4622.5 ms, number of excitations=2, field of view=3 cm, 1-mm thick axial slices perpendicular to the spinal axis, with an in-plane spatial resolution of 234 µm). RARE imaging delivers images practically free from artifacts with an appropriate phase-encoding scheme. Biological structures including tumor, with long relaxation times are the ones most sought after in clinical magnetic resonance imaging, and thus use of a long TR time with a relatively short scan time is possible with RARE sequences. It can be used to acquire images with a very high signal:noise ratio in a reasonable time by averaging. We acquired sequential BOLD fMR images first while the mouse was breathing room air followed later by carbogen (93% $O_2$_7% $CO_2$, for 9 minutes) using a GE CSI 4.7T/33 cm imaging spectrometer (GE NMR Instruments, Fremont, Calif.) incorporating AVANCE digital electronics (Biospec platform with Paravision 2.1 operating system, Bruker Medical, Billerica, Mass.). For processing fMR data, a customized and interactive fMR module was developed and interfaced to a commercially available three-dimensional image analysis package (AnalyzePC Version 5, Biomedical Imaging Resource, Mayo Clinic). A functional map was subsequently calculated pixel-by-pixel for regions visually identified as containing tumor. fMR image intensity changes from pre- and postcarbogen-paired T2-weighted magnetic resonance images were calculated with the following equation: % signal intensity change_ [(post_pre)/(pre)]_100, where "pre" refers to the T2-weighted images obtained with the mice breathing room air, and "post" refers to images acquired while breathing carbogen. To serve as a control, functional maps were obtained from back-to-back scans while the animal breathed room air to ensure pre/post image changes were nonrandom. To aid in visualization of regions of change, a color lookup table was applied to the functional map and an anisotropic diffusion filter (iterations=6, time interval=0.25) and low-pass filter (kernel 3×3×1) were applied to reduce systemic noise while preserving gross areas of change from baseline. The colorized functional map was then overlaid on a T1-weighted scan to localize areas of signal intensity change. In resultant BOLD fMR maps, minimum or no change was depicted as "green" whereas regions with net-positive change from baseline values were depicted as "blue-purple" (50 being the highest positive change), and regions with net-negative change are depicted as "yellow-red" (_50 of lookup table being the largest negative change) as illustrated. Regions of different fMR image signal intensity changes were compared for correlation with MVD count for that region.

Figure 2:
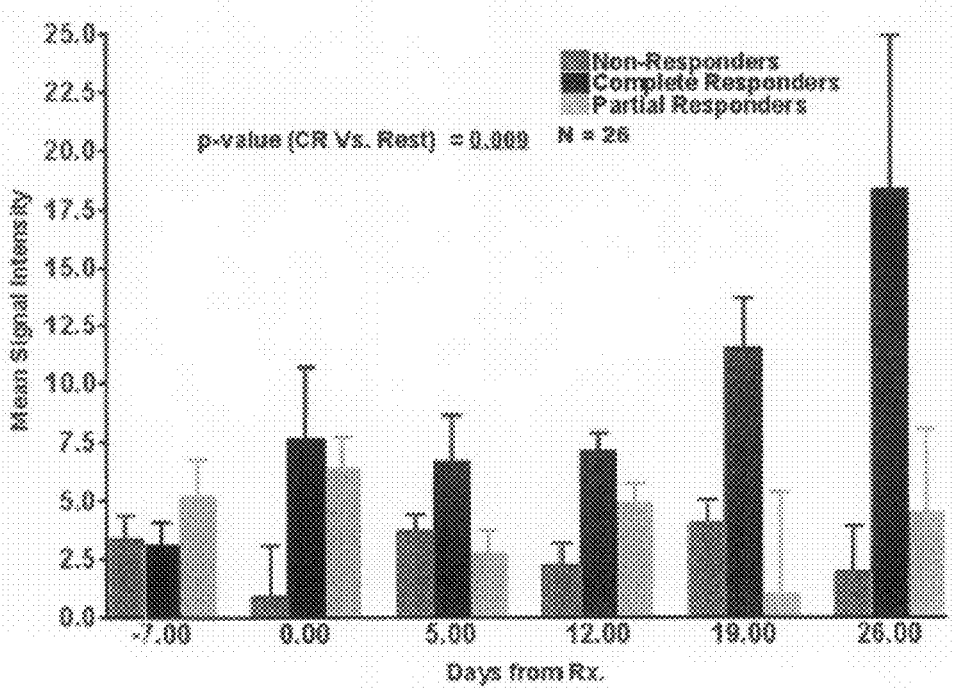
FIG. 2. A253 Response to MSC+CPT-11 Rx: Responders Vs. Partial/Non-Responders

The results are shown in FIG. 2. Increase in mean tumor fMR signal intensity reflecting a more 'normalized' vasculature is seen early on in therapy (day 5) in the complete responder as compared to the other groups.

EXAMPLE 3

This Example demonstrates the use of DCE MR imaging to delineate changes in tumor vascular perfusion and permeability as a consequence of selenium induced tumor vascular maturation. FaDu xenograft bearing mice were used. MSC was administered for 14 days. Mice were imaged using a 4.7-T/33-cm horizontal bore magnet (GE NMR Instruments, Fremont, Calif.) incorporating AVANCE digital electronics [Bruker Biospec, ParaVision 3.0.2 OS); Bruker Medical, Billerica, Mass.], a removable gradient coil insert (G060; Bruker Medical) generating a maximum field strength of 950 mT/m, and a custom-designed radiofrequency transreceiver coil. Animals were anesthetized before imaging with a ketamine/xylazine mixture (10:1) at a dose of 1.0 ml/100 mg, secured in a mouse coil chamber, and positioned on a scanner. The animals were kept warm in the magnet using a circulating water bath maintained at 37 jC. Data acquisition consisted of a localizer, T1-weighted MR images, and T2-weighted MR images. Anatomic coverage included the tumor, kidneys, and muscles. In addition, a signal-to-noise calibration standard (phantom containing a known concentration of contrast agent) was placed in the field of view (FOV) to normalize signal intensity (SI) values obtained from different animals over time. A series of three preliminary noncontrast enhanced images, with repetition times (TR) ranging from 360 to 6000 milliseconds, was acquired before an intravenous bolus injection of the contrast agent for the determination of regional precontrast T1 relaxation values. Following these baseline acquisitions, albumin-GdDTPA (0.1 mmol/kg) was introduced manually through tail vein injection, and a second series of five postcontrast images was serially obtained for ~45 minutes (day 1). T1 relaxation rates were determined using a saturation recovery, fast spin echo sequence with an effective echo time (TE) of 10 milliseconds, and a TR ranging from 360 to 6000 milliseconds [FOV=32×32 mm, slice thickness=1.0 mm, matrix size=128×96 pixels, number of excitations (NEX)=3]. Following image acquisition, animals were allowed to recover. and 30 mg/kg DMXAA was injected intraperitoneally in a volume of 0.2 ml of 0.5% sodiumbicarbonate in distilled water. Twenty-four hours after DMXAA administration, a second set of images was acquired with an identical imaging protocol as that on day 1. The mice then received a second injection of albumin-GdDTPA at the same dose, and imaging was performed for ~45 minutes after contrast agent administration, as before. On completion of image acquisitions, mice were humanely sacrificed, and tumors were excised for immunohistochemistry and histology.

Image processing and analysis were carried out using commercially available software (ANALYZE PC, Version 5.0; Biomedical Imaging Resource, Mayo Foundation, Rochester, Minn.) (Matlab's curve-fitting toolbox, Matlab Version 7.0; Math Works, Inc., Natick, Mass.). Regions of interest (ROI) of tumors, kidneys, and muscle tissues were manually drawn in the images and object maps of the ROI constructed. SI values from different ROI were obtained and used to calculate tumor enhancement (E) [22,23]. SI values were corrected for temporal variation in the spectrometer by normalizing to the phantom. Percent tumor enhancement (E) was then calculated from relative intensity (RI)

$RI = SItumor/SIphantom$ in precontrast and postcontrast images and reported as percent enhancement using the formula $$E = [(RIpost - RIpre)/RIpre] \times 100\%$$

Tumor T1 relaxation rates (R1=1/T1) were calculated from serially acquired images obtained before and after the administration of albumin-GdDTPA. Precontrast and postcontrast R1 values were calculated as previously described. To calculate DMXAA-induced changes in vascular volume and permeability, the change in longitudinal relaxation rate DR1 was calculated over time by subtracting the average precontrast R1 value from each of the five serially acquired postcontrast R1 measurements. DR1 values were reported as a function of time before and after DMXAA treatment. The slope of the DR1 series was used as a measure of vascular permeability, and Y-intercept was used to estimate vascular volume.

Figure 3:
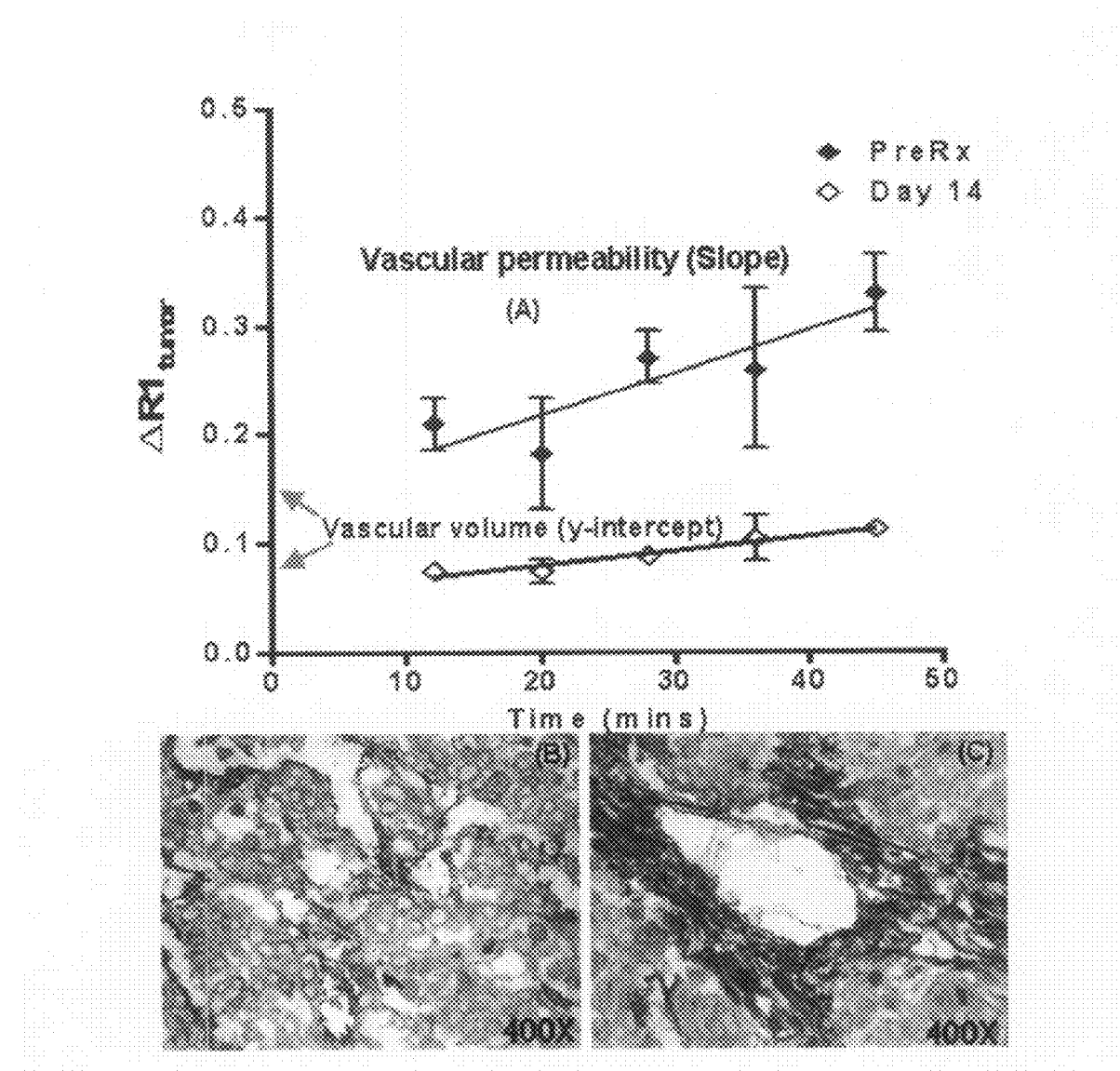
FIG. 3. Tumor (A) R1-rates before and after MSC treated tumors, determined by contrast-enhanced MRI. Double stained (CD31-red/alpha smooth muscle actin-brown) sections control (B) and MSC-treated (C) FaDu tumors after 14 days of MSC treatment.

As shown in FIG. 3, statistically significant change in terms of vascular leakiness, i.e. permeability, determined by the change in T1-relaxation rate of tumor tissues over time post MR contrast agent (Albumin-GD-DTPA, molecular weight 94 Kda) administration was seen between volume matched control and MSC treated (14 days) FaDu xenografts. MSC treatment results in reduction of tumor vascular leakiness as reflected by the slope of the ΔR1 values in FaDu xenografts. This could be a result of tumor vascular maturation as determined by the double immunohistochemical staining for the pan endothelial cell adhesion molecule (PECAM; CD31) and α-SMA in control and MSC treated mice (Day 14 of MSC treatment). Increased pericyte recruitment (brown) is seen in the tumor vasculature (pink) and the stroma as a result of MSC treatment (FIGS. 3B and 3C).

EXAMPLE 4

Figure 4:
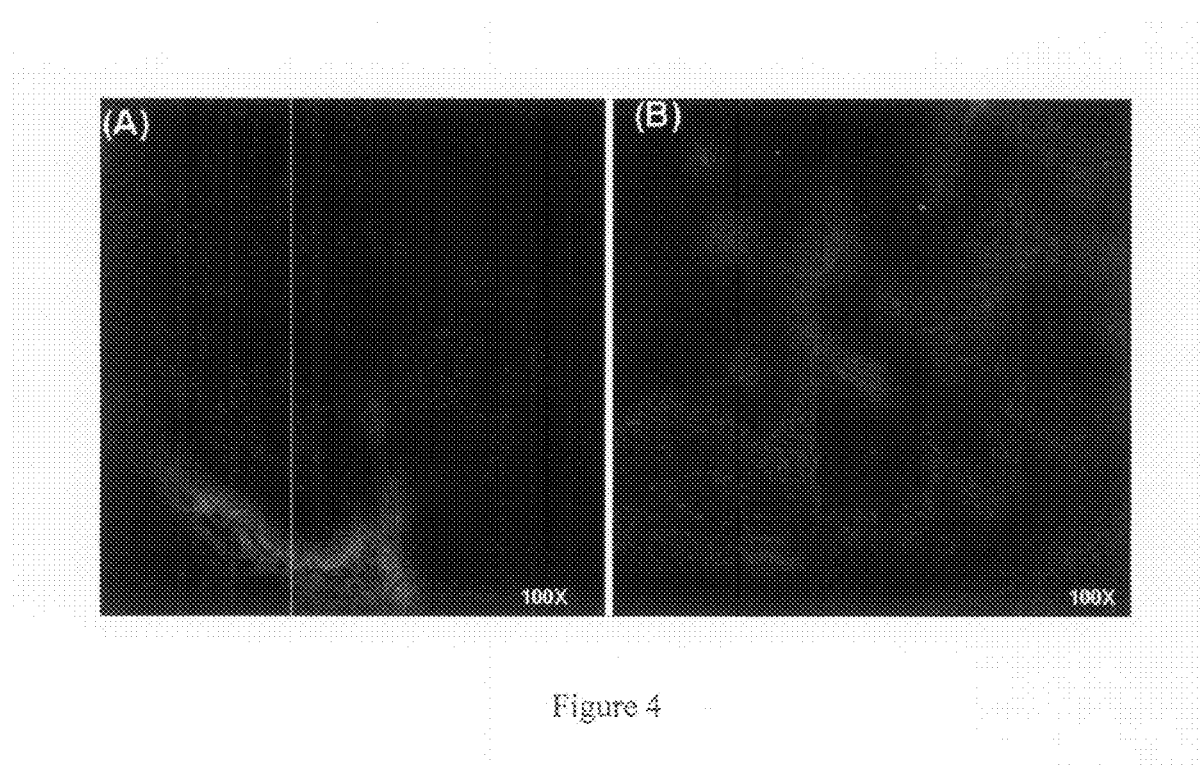
FIG. 4. Effect of MSC on tumor vascular flow. Untreated FaDu (A) shows uptake of Hoechst 33342 (blue) except some peritumoral vessels that show also an uptake of $DiOC_7$ (green). After treatment with MSC for 14 days, most FaDu vasculature (B) show uptake of both dye-evidence for better functioning 'normalized' vasculature FIG. 5. Tumor vascular maturation and normalization by MSC FIG. 6A. SN-38 concentrations in tumor and normal tissue day 14 after treatment with irinotecan alone or in combination with MSC FIG. 6B. Effect of MSC on Tumor Doxorubicin Uptake FIG. 7. Treatment schedules for MSC/ironotecan FIG. 8. Angiogenic markers regulated by MSC FIG. 9 3D whole body Magnetic Resonance (MR) angiography of control (A) and MSC-treated mice (B)

This Example demonstrates that MSC induces vascular maturation in xenografts as detected using fluorescent dyes Hoechst 33342 and $DiOC_7$. Initial studies on uptake of fluorescent dyes Hoechst 33342 (i.v at 15 mg/kg in sterile phosphate buffered saline) followed 20 minutes later with $DiOC_7$ (i.v. at 1 mg/kg in dimethyl sulfoxide) in mice bearing A253 and FaDu xenografts are indicative of tumor vascular maturation by MSC. Uptake of both dyes is indicative of functional vasculature while uptake of only one dye is indicative of abnormally functional vasculature. As depicted in FIG. 4, approximately 80% of FaDu vasculature post 14 days MSC treatment showed 'normalized' functional vasculature indicated by uptake of both the dyes as against only approximately up to 20% in the untreated control FaDu xenografts. Abnormal vasculature shut off when challenged with dyes similar to Hoechst 33342 while blood flow through 'normalized' vasculature is not affected.

EXAMPLE 5

Figure 5:
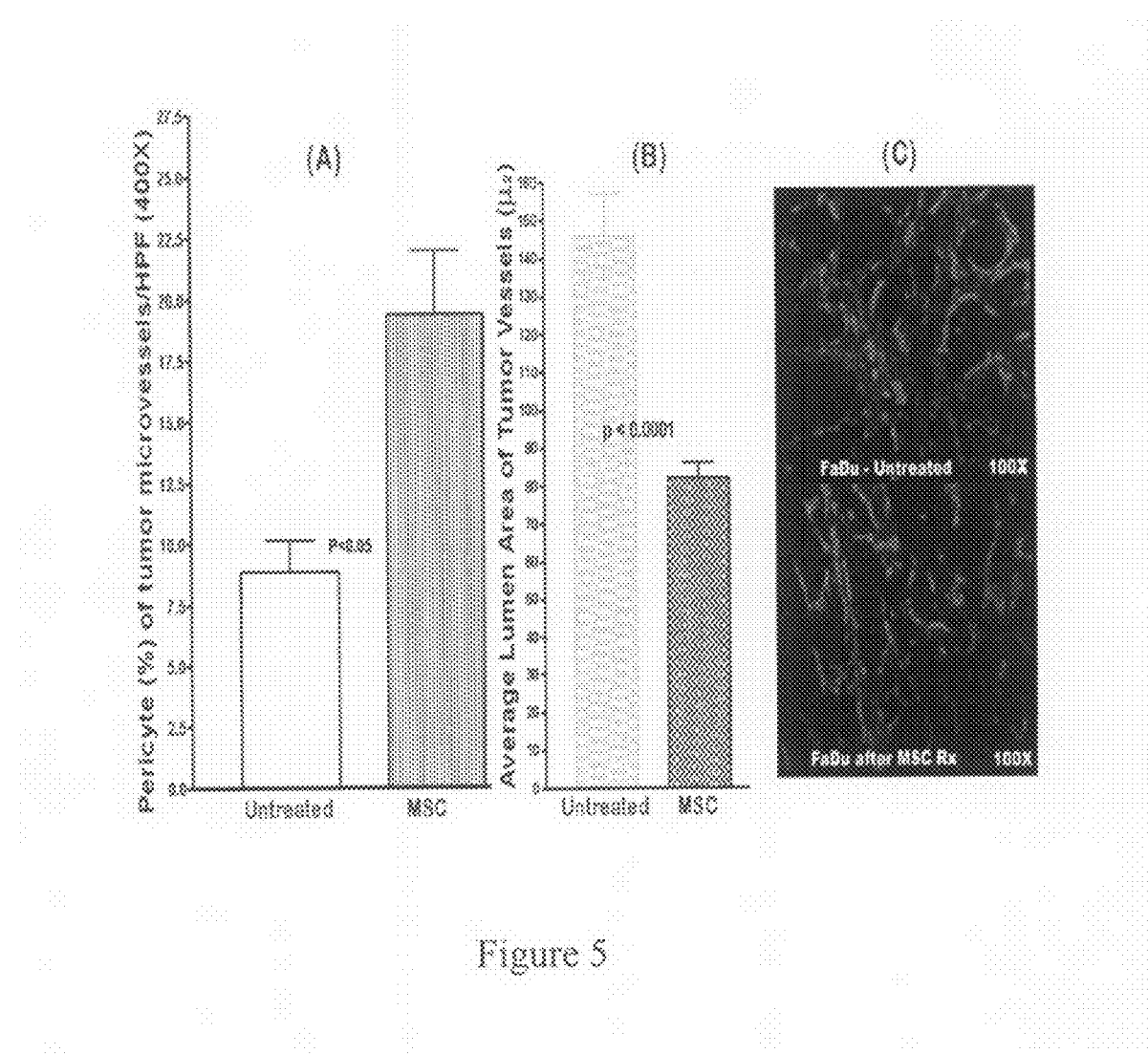

This Example demonstrates that administration of MSC results in maturation of neoangiogenic blood vessels as measured by pericyte (containing α-SMA) coverage and lumen area. FIG. 5A summarizes effect of MSC treatment on tumor vascular maturation index (VMI) and on the mean tumor vessel lumen area (FIG. 5B) in HNSCC xenografts FaDu and A253. MSC leads to a significant increase in VMI ($p<0.05$) and a reduction in tumor vessel area ($p<0.0001$) reflecting the effect on tumor vascular normalization when compared with untreated control tumors. FIG. 5C shows the architectural vascular arrangement from within a large tumor region in untreated FaDu and in MSC treated FaDu. Treatment with MSC makes the arrangement less chaotic and more 'normalized' in arrangement.

EXAMPLE 6

Figure 6A:
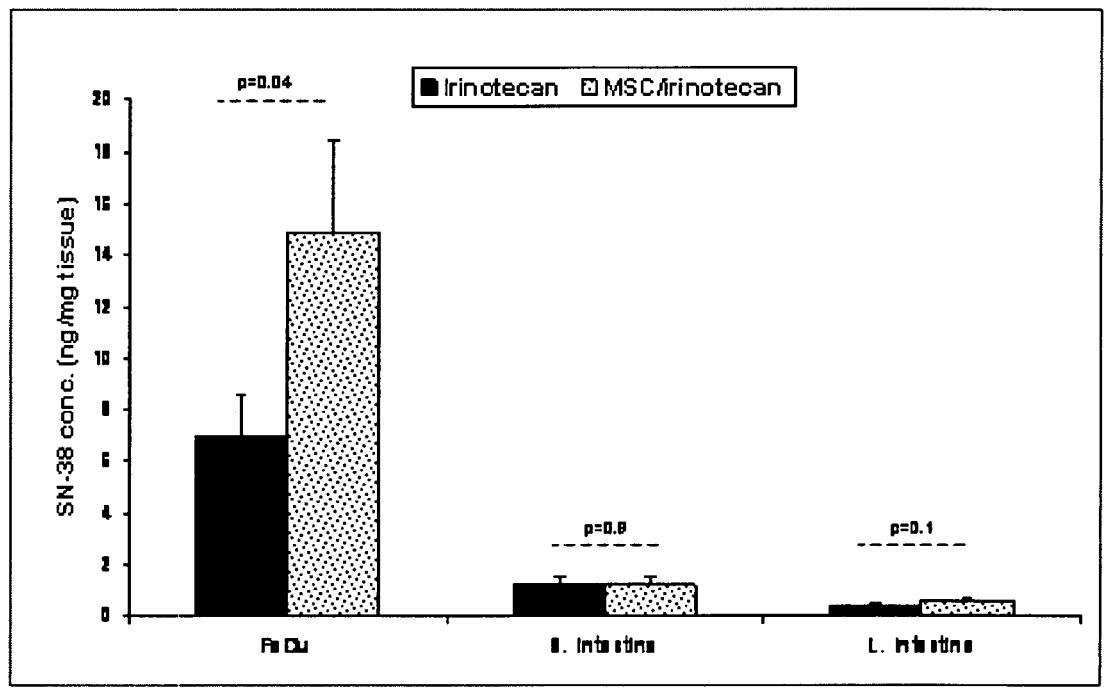
Figure 6B:
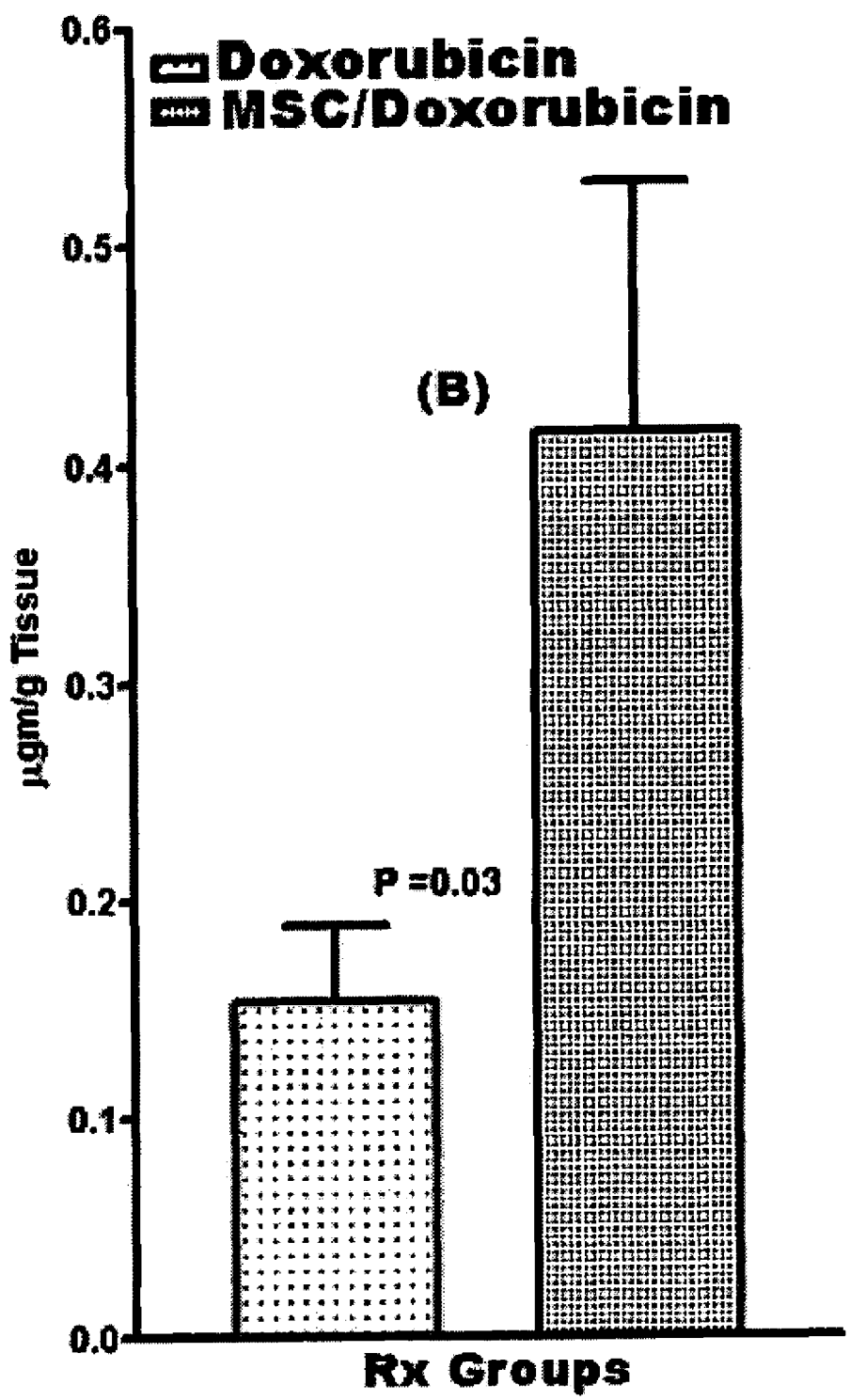

This Example demonstrates that combination therapy with MSC results in higher tumor drug uptake. FIGS. 6A and 6B show the effect of 14 days pre-treatment with MSC prior to drug administration on tumor drug uptake (2 hours post i.v.) as determined by HPLC in FaDu xenografts for CPT-11 and doxorubicin respectively. Compared to monotherapy, combination with MSC led to more than doubling of the intratumoral drug concentrations specifically in the tumor. The drug concentration in the normal tissues studied such as liver, plasma. Kidney did not show a significant increase.

EXAMPLE 7

Figure 7:
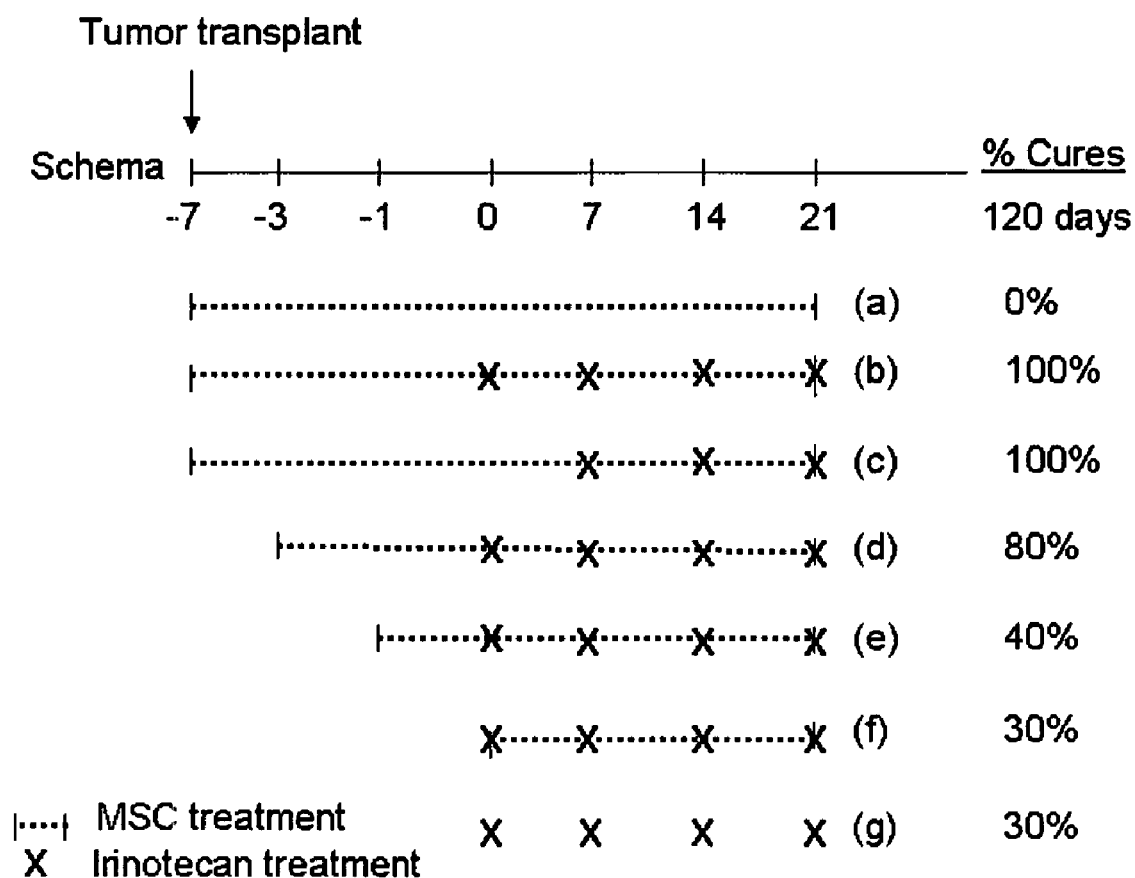

This Example demonstrates that the effect of MSC is dose and schedule dependent. As shown in FIG. 7, the therapeutic effect of selenium is dose and schedule dependent for the head and neck squamous cell carcinoma HNSCC xenograft FaDu. A minimum 7 days pretreatment with MSC is required to achieve optimal therapeutic synergy with a representative anticancer drug—irinotecan. The effect was highly selenium dose and schedule dependent. Daily pretreatment for 7-14 days was critical to achieve the selective effects of selenium. This reflects the time required for priming of tumor vasculature by MSC in order to see the therapeutic end results.

EXAMPLE 8

Figure 8:
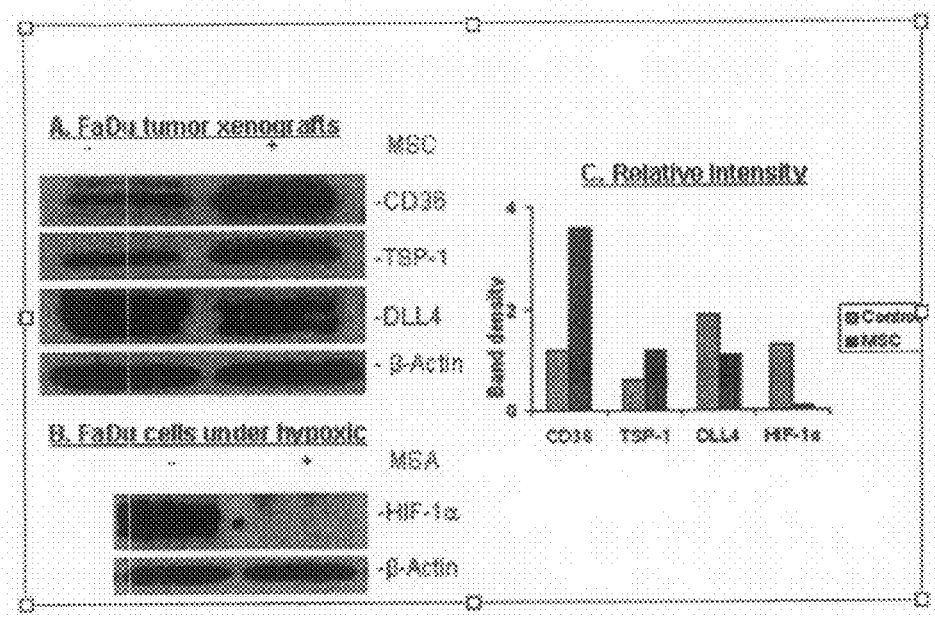

This Example demonstrates the effect of MSC on markers of angiogenesis. MSC up-regulates Thrombospondin-1 (TSP-1) a potent inhibitor of angiogenesis and important controller of tumor growth and its receptor CD36 (FIG. 8A), HIF-1α expression (FIG. 8B) and relative intensity (FIG. 8C). To assess the effects of selenium on TVM, the expression of molecular markers associated with tumor hypoxia, drug resistance and increased proliferation, namely, hypoxia-inducible factor 1α (HIF-1α), Cyclooxygenase-2 (Cox-2), inducible nitric oxide, propyl hydroxyl domain (PHD) and vascular endothelial growth factor (VEGF) were evaluated in xenograft tumors. Selenium was administered for 14 days. Western blot analysis was performed to determine the effect of MSC treatment on different antiangiogenic markers TSP-1, CD36, Delta-like 4 ligand (DLL4) and hypoxia inducible factor HIF-1α. Data in FIG. 8A indicate that CD36 is up regulated in FaDu xenografts treated with MSC. Along with the CD36 MSC up regulates TSP-1, which is known to be involved in the inhibition of angiogenesis. Further, MSC down-regulates DLL4 in FaDu xenografts. DLL4, a Notch4 ligand, was down regulated by MSC in FaDu xenograft (FIG. 8A) indicating that MSC is regulating the Notch signaling pathway to control endothelial cell differentiation which could lead to normalization the tumor vasculature.

To determine whether HIF-1α is a target for MSC, FaDu tumor cells were exposed in vitro for 24 hr to hypoxic conditions and analyzed for HIF-1α expression to FaDu cells. Exposure for 24 hr to hypoxic conditions resulted in high level of expression of HIF-1α which is not detectable under normoxic conditions. Preliminary results (FIG. 8B) indicate that selenium treatment of hypoxic cells resulted in significant inhibition of HIF-1α expression. The data in FIG. 8C is graphic representation of the relative intensity of each marker.

EXAMPLE 9

This Example demonstrates assessment of microvessel effects induced by administration of selenium using imaging techniques. Multi imaging techniques were used include preclinical magnetic resonance imaging 4.7 tunnel, intravascular imaging (IVM), fluorescence imaging (FI). These findings were confirmed using immunohistochemical techniques using CD31 and smooth muscle actin, Hoechst 33342 and DioC7.

Figure 9:
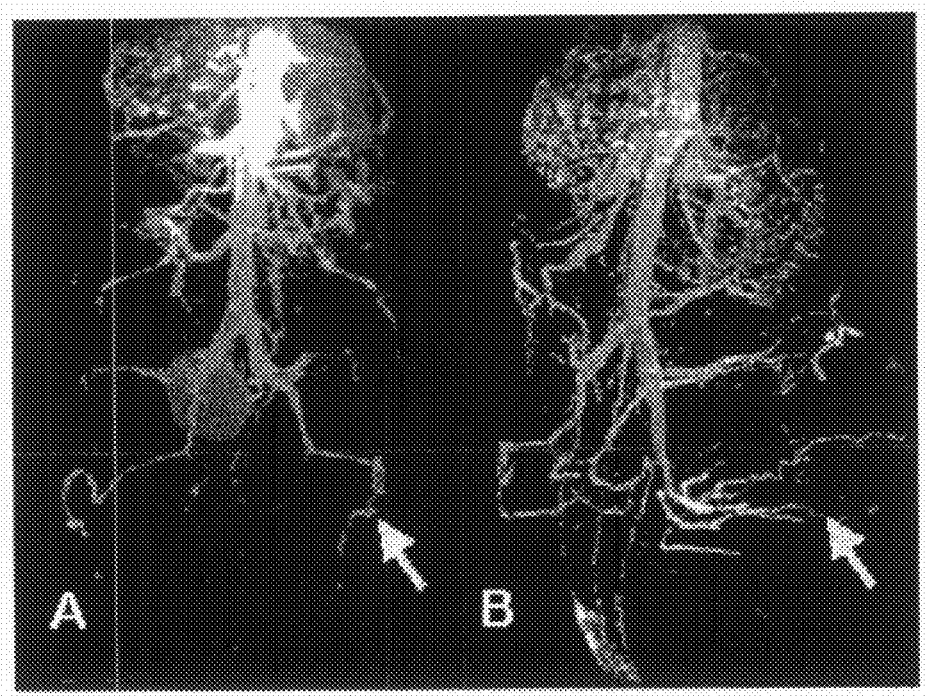

FIG. 9 present results from 3D whole body angiography MRI and provides angiographic images of control and MSC-treated tumors. Arrows indicate the location of the tumor. Untreated control mice showed tortuous feeder vessel supporting the tumor (FIG. 9A) as opposed to the vascular support post 14 days of MSC treatment (FIG. 9B).

Figure 10:
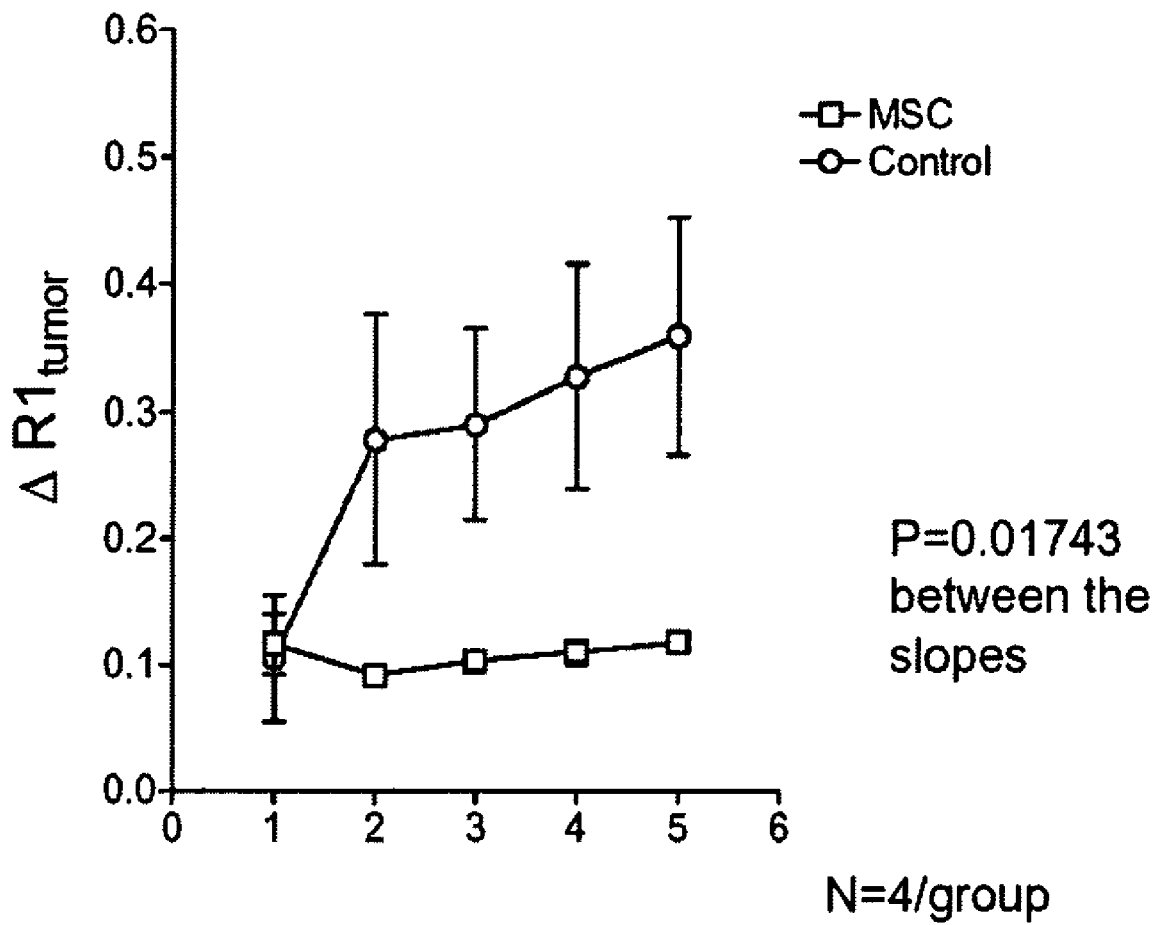
FIG. 10 Detection of tumor vascular maturation by MSC using Dynamic Contrast Enhanced-Magnetic Resonance Imaging (DCE-MRI).

The DCE-MRI results presented in FIG. 10 demonstrate the tumor vascular maturation induced by MSC. In FIG. 10, at post 14 days of MSC treatment, measurement of relaxation rates over time (R1=1/T1) revealed a statistically significant decrease in vascular volume and permeability (FIG. 10). This is in agreement with our estimates of MVD as MSC treatment does lead to a reduction in MVD. However, the decrease in permeability could be a result of the 'maturation' effect of MSC. To validate findings from the imaging studies, immunohistochemical staining for the pan endothelial cell adhesion molecule (PECAM; CD31) along with staining with alpha-smooth muscle actin was performed in control and MSC-treated mice (Day 14 after treatment). As seen in FIGS. 3B & 3C, increased staining of α-SMA in frozen tumor sections 14 days after MSC treatment was seen, indicating MSC-induced vascular maturation.

While this invention has been described through specific examples, routine modifications will be apparent to those skilled in the art and such modifications are intended to be included in the present invention.

The invention claimed is:

1. A method for inhibiting the growth of a solid tumor comprising the steps of:
   a) administering methylselenocysteine (MSC) and/or seleno-L-methionine (SLM)
   b) monitoring blood vessel maturation in the tumor; and
   c) upon detection of vessel maturation, administering a therapeutically effective dose of a chemotherapeutic agent.

2. The method of claim 1, wherein blood vessel maturation is monitored by magnetic resonance imaging.

3. The method of claim 1, wherein the blood vessel maturation is monitored by immunohistochemical techniques on a biopsy sample of the tumor.

4. The method of claim 1, wherein the MSC or SLM is administered for at least 3 days before carrying out step b.

5. The method of claim 3, wherein the MSC or SLM is administered for at least 5 days before carrying out step b.

6. The method of claim 1, wherein the chemotherapeutic agent is selected from the group consisting of irinotecan, 5-fluorouracil, taxol, cisplatin, doxorubicin, oxaliplatin, and cyclophasphamide.

7. A method for identifying tumors likely to respond to chemotherapy comprising the steps of:
   a) administering a selenium compound selected from the group consisting of methylselenocysteine (MSC) and seleno-L-methionine (SLM);
   b) monitoring an indicator of microvessel maturation in the tumor over a period of between 3-8 days after administration of the selenium compound;
   wherein an increase in the microvessel density of the tumor in response to selenium compound administration is indicative of the tumor being responsive to the subsequent chemotherapeutic agent.

8. The method of claim 7, wherein blood vessel maturation is monitored by magnetic resonance imaging.

9. The method of claim 7, wherein the blood vessel maturation is monitored by immunohistochemical techniques on a biopsy sample of the tumor.

10. The method of claim 7, wherein the MSC or SLM is administered for 3 days before carrying out step b.

11. The method of claim 7, wherein the MSC or SLM is administered for 5 days before carrying out step b.

* * * * *